(12) United States Patent
Chan et al.

(10) Patent No.: US 9,689,849 B2
(45) Date of Patent: Jun. 27, 2017

(54) COLORIMETRIC INDICATORS FOR USE IN MEDICAL DEVICES

(71) Applicant: General Electric Company, Schenectady, NY (US)

(72) Inventors: Kwok Pong Chan, Troy, NY (US); Sumeet Jain, Schenectady, NY (US); Matthew Jeremiah Misner, Delanson, NY (US); Pekka Simeon Astola, Espoo (FI); Johannes Harri Eemeli Osterberg, Helsinki (FI)

(73) Assignee: General Electric Company, Niskayuna, NY (US)

( * ) Notice: Subject to any disclaimer, the term of this patent is extended or adjusted under 35 U.S.C. 154(b) by 71 days.

(21) Appl. No.: 13/966,313

(22) Filed: Aug. 14, 2013

(65) Prior Publication Data
US 2015/0050196 A1    Feb. 19, 2015

(51) Int. Cl.
*G01N 21/75* (2006.01)
*G01N 31/22* (2006.01)

(52) U.S. Cl.
CPC .......... *G01N 31/229* (2013.01); *Y10T 156/10* (2015.01)

(58) Field of Classification Search
CPC .................... G01N 31/229; Y10T 156/10
USPC ....... 422/400, 401, 420, 421, 422, 423, 424, 422/425, 426, 427, 428, 429, 68.1, 82.05, 422/82.06; 436/164, 169, 170; 435/13, 435/283.1, 287.1, 287.7, 287.8, 287.9, 435/288.7
See application file for complete search history.

(56) References Cited

U.S. PATENT DOCUMENTS

| | | | |
|---|---|---|---|
| 3,954,011 A * | 5/1976 | Manske | 374/102 |
| 4,526,752 A | 7/1985 | Perlman et al. | |
| 5,942,438 A | 8/1999 | Antonoplos et al. | |
| 2003/0211618 A1* | 11/2003 | Patel | 436/38 |
| 2005/0113808 A1 | 5/2005 | Berndt | |
| 2005/0249899 A1 | 11/2005 | Bonutti | |
| 2006/0054526 A1 | 3/2006 | Dean et al. | |
| 2006/0069305 A1 | 3/2006 | Couvillon et al. | |
| 2007/0017042 A1 | 1/2007 | Cincotta et al. | |
| 2007/0173892 A1* | 7/2007 | Fleischer et al. | 607/2 |
| 2009/0303440 A1 | 12/2009 | Heacock et al. | |
| 2011/0137306 A1 | 6/2011 | Allen | |
| 2011/0316696 A1 | 12/2011 | Yao et al. | |

FOREIGN PATENT DOCUMENTS

JP    WO 2012132844 A1 *  10/2012 ............. B01L 3/505

* cited by examiner

*Primary Examiner* — Dennis M White
(74) *Attorney, Agent, or Firm* — Pabitra K. Chakrabarti

(57) ABSTRACT

A colorimetric time indicator configured to indicate time specificity is provided. The colorimetric time indicator includes a colorimetric layer configured to be operatively coupled to a disposable medical device. The colorimetric time indicator is configured to indicate the time specificity via one or more visual indicators upon exposure to one or more external stimuli.

16 Claims, 11 Drawing Sheets

FIG. 23(a) Device not in use
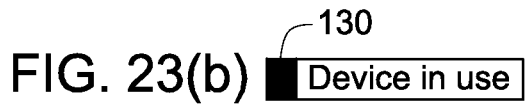
FIG. 23(b) ▉ Device in use  130
FIG. 23(c) ▉ Device in use ● 131
FIG. 23(d) ▉ Device in use ● ● 132
FIG. 23(e) ▉ Device in use ● ● ● 133
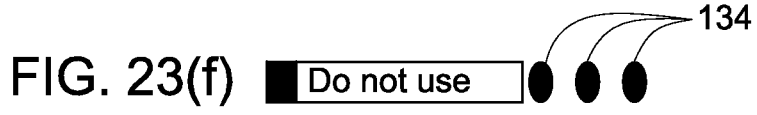
FIG. 23(f) ▉ Do not use ● ● ● 134
140
Provide a disposable medical device — 142
↓
Provide a colorimetric time indicator — 144
↓
Operatively couple the colorimetric time indicator to the disposable medical device — 146
FIG. 24

COLORIMETRIC INDICATORS FOR USE IN MEDICAL DEVICES

BACKGROUND

The invention relates to colorimetric indicators, and more particularly to colorimetric indicators for use in medical devices.

Invasive and non-invasive monitoring devices, such as, but not limited to, monitoring electrodes, are commonly used for medical applications. Such monitoring devices may or may not be reusable. For example, electrocardiograph (EEG) and electroencephalography (EEG) lead-sets may be reusable, disposable, or single patient single use devices. Reusable medical devices need to be cleaned after every patient use and also possibly during one patient stay with a defined time period.

In healthcare applications, to reduce or prevent infectious contamination, it is often desirable to provide indicators for devices, where the indicators are configured to provide signals representative of a time period for which a medical device has been in use. For example, it may be desirable to use indicators to indicate a useful life, a sanitization state, a contamination level, or an infection state of the devices. In case of multiple users, the monitoring electrodes and lead-sets may need to be cleansed after use by one patient and before use by another patient to prevent transfer of infections from one patient to another. Whereas, in case of single user, the monitoring electrodes and lead-sets may need to be cleansed and sterilized at regular intervals while being used by the same patient.

Typically, reusable and single patient use medical devices, such as, but not limited to, electrodes and lead-sets, may further cumulative infectious contamination due to the continuous contact of the device with the patient skin, body secretions, and inaccurate cleansing and disinfection. Usually, in case of single patient use devices, this infectious contamination is minimized by disposing the device after the device has been used for a determined period of time. However, existing medical devices do not provide information regarding the time period for which a particular device has been in use. The lack of information or indication regarding the use time of the medical device impairs the effect of the single patient use devices in controlling infection.

Typically, a use time of the medical device or accessory is controlled manually. Currently, a user or operator of the medical device needs to rely on instructions, warnings and cautions in user manuals, or labels on the medical device that suggest a suitable use time for that device. However, the information in the user manual regarding the use time of the device still does not provide information regarding the use time of the device. That is, the manuals do not provide information as to for how long the medical device has been in use. Further, reading the instructions regarding the use time and following the instructions are dependent on the operator, attendant or physician tending to the patient. Moreover, currently, it is not self-evident if the medical device has been in use previously or is new. For example, in case of ECG electrodes, it is difficult to determine whether the accessory is used or unused, or an amount of time for which the accessory has been in use. Lack of such indicators or information may adversely affect the use of medical devices for infection control.

BRIEF DESCRIPTION

In one embodiment, a colorimetric time indicator configured to indicate a time specificity is provided. The colorimetric time indicator includes a colorimetric layer configured to be operatively coupled to a disposable medical device. The colorimetric time indicator is configured to indicate the time specificity via one or more visual indicators upon exposure to one or more external stimuli.

In another embodiment, a disposable medical device having a colorimetric time indicator is provided. The colorimetric time indicator includes a substrate and a colorimetric layer disposed on the substrate. The colorimetric layer is configured to change at least one visible parameter upon exposure to one or more external stimuli. Further, the colorimetric layer is configured to indicate time specificity via one or more visual indicators upon exposure to the one or more external stimuli.

In yet another embodiment, a method that includes providing a disposable medical device, providing a colorimetric time indicator, and operatively coupling the colorimetric time indicator to the disposable medical device is presented.

DRAWINGS

These and other features and aspects of embodiments of the invention will become better understood when the following detailed description is read with reference to the accompanying drawings in which like characters represent like parts throughout the drawings, wherein.

Figure 1:
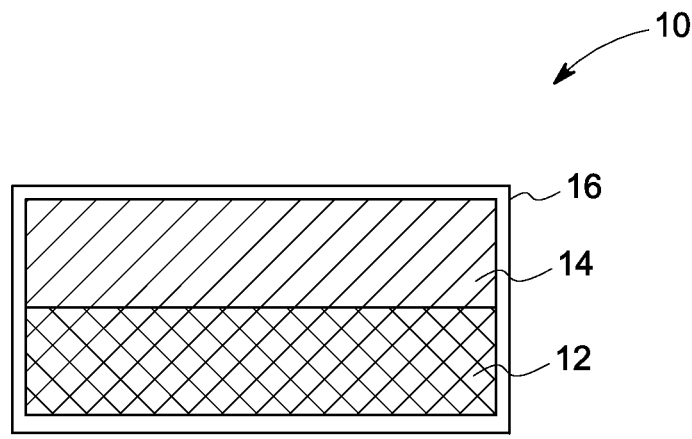
FIGS. 1-2 are cross-sectional views of an example colorimetric indicator, in accordance with aspects of the present disclosure.

FIGS. 23(a)-(f) are schematic representations of an example of a gradual color change in a disposable medical device employing a colorimetric time indicator, in accordance with aspects of the present disclosure; and FIG. 24 is a flow chart for an example method for providing a medical device having a colorimetric time indicator.

DETAILED DESCRIPTION

Typically, in healthcare applications, medical devices or accessories that are configured for disposable, short term use or single patient use are often prone to being used past desirable time limits, or number of users. In case of overuse of the medical devices or accessories, the medical devices or accessories may inadvertently act as a medium for infectious contamination. For example, infectious contamination may result due to extended physical contact, e.g., contact of the devices with a skin of the patient, or exposure to secretions, such as sweat.

While, medical devices configured for a single patient use may have relatively lower risk of infectious contamination as compared to medical devices for multiple patients, however, in the medical devices for the single patient use the probability of contamination may arise due to use of the devices beyond the defined or desirable usage time. Existing medical devices for single or multiple patients do not include an indicator that may provide an indication regarding the usage time of the device. By way of example, the existing devices do not provide information regarding a time period for which the device has been in use, or if the device has been used for a period beyond the intended usage period of the device.

In certain embodiments, a colorimetric time indicator configured to indicate time specificity is provided. It should be noted that the terms "colorimetric time indicator" and "colorimetric indicator" may be used interchangeably throughout the application. The colorimetric time indicator may be configured to indicate the time specificity via one or more visual indicators upon exposure of the colorimetric time indicator to one or more external stimuli is provided. The colorimetric indicator includes a colorimetric layer. The colorimetric layer may be made of one or more colorimetric materials. The colorimetric materials are configured to react with external stimuli in a time specific manner. As used herein, the term "time specificity" refers to a time interval from the time when the use of the medical device is commenced to the time when the usage time of the device has elapsed. By way of example, for a medical device having a usage time of about 24 hours, the colorimetric time indicator is configured to indicate a time specificity from the time the use of the medical device is commenced (0 hours) to up to about 24 hours. The gradual progression of time from 0 hours to about 24 hours may be represented using the time specificity as represented in FIGS. 7-22. In one example, the time specificity may refer to a single time period indicative of the use of an ECG electrode. In another example, the time specificity may refer to a plurality of time periods indicative of different stages in the use of the disposable medical device. It should be noted that there may be a time gap between the time when the use of the medical device is commenced and when a visible change begins to show in the colorimetric time indicator. This lag in time in the visible change beginning to show in the indicator may or may not be intentional. The time of reaction of the colorimetric material with the external stimuli may primarily depend on the chemical composition of the colorimetric material. In some embodiments, the time specificity of the colorimetric layer may be tailored or modified. Furthermore, in some of these embodiments, tunability of the time specificity may be facilitated by the use one or more buffer agents. The one or more buffer agents may be disposed at least in part in the colorimetric layer. In one example, the buffer agents may include reducing buffer agents.

Also, as used herein, the term "external stimuli" refers to a stimuli external to the colorimetric indicator or the medical device, where the external stimuli is configured to react with the colorimetric material to provide the visual indicators. Non-limiting examples of the external stimuli may include one or more of oxygen, carbon dioxide, moisture, ambient light, or combinations thereof. In one example where oxygen is the external stimuli, the oxygen may be received by the colorimetric indicator from ambient air, ambient moisture, or both.

In addition, as used herein, the term "visible indicator" refers to a physical change in the colorimetric time indicator that is visible to a naked human eye. In one embodiment, a label color on the medical device, such as, but not limited to, a grabber or snap type connector may change from one color to another due to exposure to the external stimuli. In one embodiment, the colorimetric time indicator may be disposed in or on the label attached to the medical device. In an alternative embodiment, the colorimetric time indicator may be an integral part of the medical device. Non-limiting examples of the visual indicator may include a color change of the colorimetric layer, a visible change in dimensions or shape of the colorimetric layer, or both.

In some embodiments, the colorimetric time indicator may be disposed on the medical device. The colorimetric time indicator may be in a passive stage when the device is not being used. Subsequently, the colorimetric time indicator may be in an active stage when the device is being used. The transition from the passive stage to the active stage may be initiated immediately or after a determined time upon exposure of the indicator to the external stimuli. As used herein, the term "passive stage" refers to a stage of the colorimetric indicator where the indicator is not exposed to the external stimuli. Accordingly, in the passive stage the indicator does not provide any time specificity. As used herein, the term "active stage" refers to a stage of the colorimetric indicator, where the indicator is exposed to one or more external stimuli. Accordingly, in the active stage the indicator is configured to provide an indication of a time elapsed from the time the medical device has been in use. In one example, in the active stage the colorimetric indicator may be configured to change color upon exposure to one or more external stimuli. Moreover, in one example, the colorimetric indicator may be configured to indicate duration of time for which the device has been in use. In another example, the colorimetric indicator may be configured to indicate whether the device is suitable for further use, or has passed its usage time.

Furthermore, in certain embodiments, the colorimetric layer of the indicator may be disposed on at least a portion of the medical device. For example, the colorimetric layer may be disposed on at least a portion of a lead set cable, or the entire length of the cable. In some embodiments, the colorimetric indicator may be disposed on disposable medical devices, where the medical devices need to be substituted, replaced, removed, or monitored after a determined period of time or at regular intervals. By way of example, the colorimetric indicator may be disposed on disposable medical devices to indicate expiration of useful life.

As used throughout the application, phrases "medical device" or "medical devices" may include both medical devices as well as accessories associated with such devices.

Non-limiting examples of such medical accessories may include lead cables and electrodes. Non-limiting examples of medical devices that may employ the colorimetric indicator may include one or more of monitoring and/or diagnostics devices, such as, but not limited to, devices for monitoring and diagnosing cardiac function; blood circulation devices for measuring non-invasive blood pressure (NIBP), invasive blood pressure (IBP), body temperature, oxygen saturation (e.g., oxygen return saturation ($SvO_2$) and oxygen delivery saturation ($SpO_2$)); hemoglobin measurement devices; anesthesia delivery devices; devices for monitoring or determining brain functions (e.g. devices for measuring a level of hypnosis); and devices for measuring vital parameters pertaining to body functions.

In one embodiment, monitoring and/or diagnosing cardiac functions may include electrocardiograph (ECG), radiotranslucent ECG, X-ray, and magnetic resonance imaging (MRI). Non-limiting examples of disposable medical devices associated with monitoring and/or diagnosing cardiac functions may include cables, lead-wires, electrodes, papers for monitors and recorders. Non-limiting examples of disposable medical devices used for monitoring and/or diagnosing various other functions may include cuff and hose for NIBP, blood pressure transducer set, cardiac output set (e.g., catheter), body fluid heating unit and associated accessories. Non-limiting examples of medical devices associated with ventilator mechanics may include a breathing bag, a tube, an anesthesia mask, endotracheal tubing, an absorber, a filter, and a humidifier. Also, non-limiting examples of medical devices associated with spirometry applications may include devices, such as, but not limited to, spirometry tubing, a gas flow sensor, or both. Non-limiting examples of medical devices used in airway mechanisms may include a main stream sensor, a side stream sensor, an airway adapter, a carbon dioxide mask, a water-trap, a gas sampling line, an exhaust line for scavenging, a nasal cannula, and a laryngoscope blade. In one embodiment, the colorimetric indicator may be disposed on a disposable medical cable, such as, but not limited to, a flat cable or a round format cable for the medical device.

Advantageously, the colorimetric time indicator is cost effective and easy to use. In certain embodiments, the colorimetric time indicator may facilitate avoiding undesirable extended use or multiple patient use of medical devices that are intended for single patient use, short term use, or single time use (disposable). The present application may facilitate at least partially preventing patients as well as institutions, such as, but not limited to, hospitals, nursing homes from incurring additional costs and discomfort otherwise caused due to hospital acquired infections (HAI), cross contaminations, or both. Moreover, advantageously, the colorimetric indicator enables improvement of the quality of care by ensuring proper use of devices in clinical, home and any other monitoring environment. In some embodiments, the colorimetric indicator may facilitate reduction in false alarms and provide efficient alarm management. In one example, the colorimetric indicator is configured to function as a visual alarm. In certain embodiments, the colorimetric indicators are configured to provide a simple visual indication representative of a need for replacement of the disposable medical device. Advantageously, the colorimetric indicator employs one or more colorimetric materials such that other chemicals, such as, but not limited to, hospital used disinfectants, do not interfere with the colorimetric indicator. In certain embodiments, the colorimetric layer may be a biocompatible material according to ISO 10993-5 and -10 standards.

In certain embodiments, the colorimetric indicator may be at least partially disposed in a packaging. In one embodiment, the medical device and the indicator may share the same packaging. In another embodiment, the medical device and the indicator may be packed in a different packaging. In one example, a portion of the medical device may be configured to act as a packaging for the indicator. In some embodiments, the packaging may be configured to provide an environment that is substantially free of the external stimuli. By way of example, in case of oxygen activated colorimetric indicator, the packaging may be configured to provide an environment (for the colorimetric indicator) that is substantially free of oxygen. In this example, when the packaging is removed from the indicator, depending on the time specificity, the indicator subsequently attains an activated state upon coming in contact with the ambient oxygen present in the surrounding air. In some embodiments, the packaging may be made from a plastic material, such as any common plastic material configured to prevent exposure of the colorimetric indicator to the external stimuli when the indicator is disposed in the packaging. In some of these embodiments, protective plastic bags or packaging may be disposed around the colorimetric indicator or only the colorimetric layer. In a non-limiting example, vacuum packaging may be performed for the whole product or just for the portion of the medical device or the colorimetric indicator where the colorimetric layer is disposed.

Furthermore, in certain embodiments, the medical devices, such as disposable medical devices, may be pre-fitted with a colorimetric indicator. In certain other embodiments, the medical devices may not be pre-fitted with the colorimetric indicator. In these embodiments, the colorimetric indicator may be coupled to the medical device prior to employing the medical device for its intended use. In one example, the colorimetric indicator may be coupled to the medical device immediately prior to employing the medical device. Alternatively, the colorimetric indicator may be coupled to the medical device ahead of time, and not immediately prior to employing the medical device.

By way of example, the colorimetric indicator may be in the form of a sticker label that may be readily disposed on a medical device. In this embodiment, the colorimetric indicator may be taken out of the packaging and the colorimetric layer of the indicator may be exposed to the ambient air and/or moisture, immediately before disposing the colorimetric indicator on a medical device. Further, the colorimetric indicator may be easy to dispose on different medical devices, surfaces and materials. In one embodiment, colorimetric indicator may be configured to be easily attachable to all disposable, short term use or single patient use ECG accessories. In one example, depending on the type of ECG lead wires, the medical device may employ two or more colorimetric indicators to track two or more different time periods (e.g., such as, but not limited to, a usable period of e.g., 1, 3, 7 or 14 days). In another example, the usable period may be with regard to a single patient use (SPU). In this example, once the indicator is exposed to the external stimuli, the indicator may provide a visual indication instantly. In another example, the colorimetric indicator may be used to prevent using a medical accessory of a medical device by multiple users, such as, but not limited to ECG lead set. In this example, when the colorimetric indicator is taken out of the packaging, the indicator may be configured to instantly indicate a color change. In some embodiments, the colorimetric indicator may be used to avoid the use of a disposable and short term use ECG lead wires after a desirable useful period of the lead wires. In these embodiments, the color change in the indicator may be gradual.

Non-limiting examples of colorimetric materials for the colorimetric layer may include oxygen sensitive dyes, carbon dioxide sensitive dyes, ambient light sensitive dyes, or combinations thereof. Also, non-limiting examples of suitable oxygen sensitive dyes may include one or more of erioglaucine disodium salt, indigo carmine, or Fast Green FCF. In one embodiment, a reduced form of an erioglaucine disodium salt turns intense blue from light yellow upon contact with air. In another embodiment, a reduced form of indigo carmine turns from light yellow to intense blue upon contact with air. In one embodiment, a reduced form of fast green FCF reduces from light yellow to intense green upon contact with air.

In certain embodiments, a time specificity of the colorimetric layer may be tuned using one or more buffer agents. In some embodiments, an amount of the buffer agent may be determined based on a desirable reaction time of the colorimetric layer. By way of example, for a medical device configured for a single patient use, the colorimetric indicator may use a colorimetric layer that has a short reaction time, such that the colorimetric indicator may indicate a color change immediately upon being taken out of the packaging. In another example where it is desirable to specify number of days for which the medical device has been used, the colorimetric layer may be configured to have a relatively long reaction time. For example, the colorimetric layer may change color after 24 hours to indicate that the medical device has been in use for 1 day.

Additionally, in certain embodiments, a time specificity of a colorimetric layer may be tunable from hours to over a week. In some embodiments, the colorimetric indicator may include a barrier layer. In one example, the barrier layer may be used in addition to a buffer agent. In another example, the barrier layer may be used without the buffer agent. In some embodiments, the barrier layer alone, or in combination with the buffer agent, may be configured to facilitate tenability of the time specificity of the colorimetric time indicator. By way of example, the barrier layer may be configured to delay the reaction time of the colorimetric layer, or the colorimetric layer and the buffer agent, to a desirable amount.

Non-limiting examples of materials for the barrier layer may include plastic films. In certain embodiments, a thickness and material of the barrier layer may depend on a permeability rate of the external stimulus for the barrier layer. Non-limiting examples of the plastic material may include polyester, poly-vinylidene choride, poly(methyl methacrylate) (PMMA), polycarbonate, polystyrene, polyolefin, or combinations thereof.

Moreover, non-limiting examples of the buffer agents may include ascorbic acid, reducing saccharides (e.g., glucose), ferrous citrate, E301 sodium ascorbate, E302 calcium ascorbate, E303 potassium ascorbate, or combinations thereof.

In one embodiment, the colorimetric time indicator may be configured to transition from a passive state to an active state upon being exposed to an activating media, such as, but not limited to, gamma radiation, ultraviolet radiation, plasma, ethylene oxide, or combinations thereof. The activating media may be provided in addition to the external stimulus.

Figure 2:
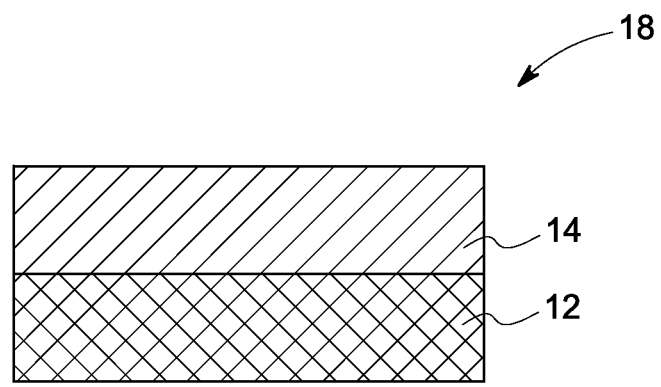

FIGS. 1 and 2 illustrate cross-sectional views 10, 18 of an example colorimetric indicator 10. In the illustrated embodiment of FIG. 1, the colorimetric indicator 10 is disposed in a packaging 16. When in the packaging 16, the indicator 10 is in a passive state. In the illustrated embodiment of FIG. 2, the packaging 16 is removed from the indicator 10 to transition the indicator 10 from the passive state to an active state. Reference numeral 18 may be used to represent a portion of the indicator 10 in the active state. The packaging 16 may be removed before operatively coupling the colorimetric indicator 10 to a disposable medical device. In the illustrated embodiments of FIGS. 1 and 2, the colorimetric indicator 10 includes an adhesive material 12 that facilitates disposing the colorimetric indicator 10 on a medical device (not shown). Non-limiting examples of the adhesive material 12 may include poly-oxymethylene (POM), thermoplastic polyurethane (TPU), or others. The colorimetric indicator 10 further includes a colorimetric layer 14 having one or more colorimetric materials. Although not illustrated, in some embodiments, the adhesive material 12 may not be disposed in the packaging 16. In these embodiments, only the colorimetric layer 14 may be disposed in the packaging 16. In some embodiments, a portion of the adhesive material 12 may be disposed in the packaging 16. The adhesive material 12 may be in the form of a continuous layer, a continuous pattern, a discontinuous pattern, or combinations thereof.

In some embodiments, the packaging 16 may be made of a material that is configured to provide an environment that is substantially free of the external stimuli. It should be noted that an environment substantially free of the external stimuli refers to an environment, which does not result in any visual indication in the colorimetric layer 14. In one example, the packaging 16 provides an environment that is substantially free of oxygen. In this example, at least a portion of the colorimetric indicator 10 may be packaged in a non-oxygenated environment. By way of example, at least the colorimetric layer 14 of the indicator 10 may be disposed in a non-oxygen environment.

Figure 3:
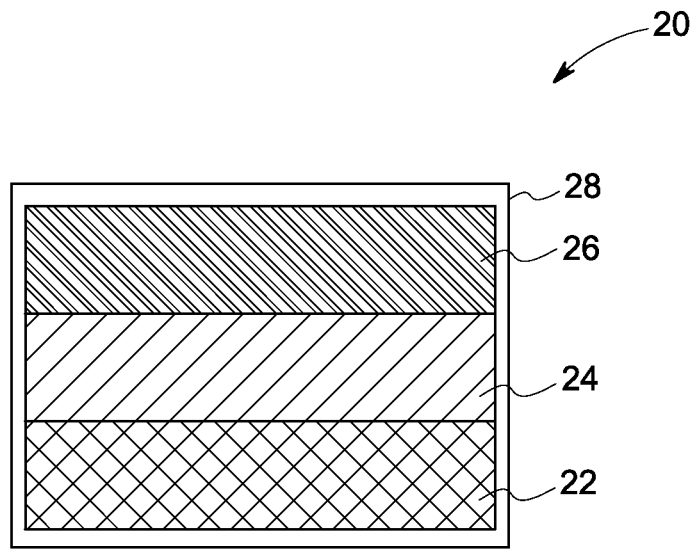
FIGS. 3-4 are cross-sectional views of another example of a colorimetric indicator, in accordance with aspects of the present disclosure.
Figure 4:
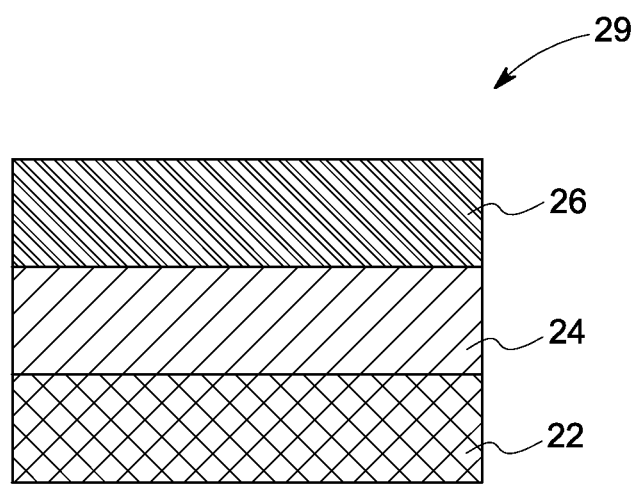

FIGS. 3-4 illustrate another example of a colorimetric time indicator of the present application. In the illustrated embodiments of FIGS. 3-4, the colorimetric indicator 20 includes an adhesive 22, a colorimetric layer 24, and a barrier layer 26. The barrier layer 26 may be configured to modify a reaction time of the colorimetric layer 24 to a desirable extent to provide desirable time specificity to the colorimetric indicator 20. As illustrated in FIG. 3, the colorimetric indicator 20 may further include a packaging 28. The packaging 28 may be configured to provide an environment to the colorimetric layer 24 and the barrier layer 26, where the environment is substantially free of the external stimuli. FIG. 4 is representative of the colorimetric indicator without the packaging 28 and may be generally represented by reference numeral 29. As illustrated in FIG. 4, the packaging 28 may be removed to allow the portion 29 of the colorimetric indicator 20 to respond to the external stimuli to start the active stage of the colorimetric indicator 20. The packaging 28 may be removed immediately before or after disposing the indicator 20 on the medical device. Alternatively, if the indicator 20 is pre-fitted on the medical device, the packaging 28 may be removed immediately before or after the indicator 20 is brought in use.

Figure 5:
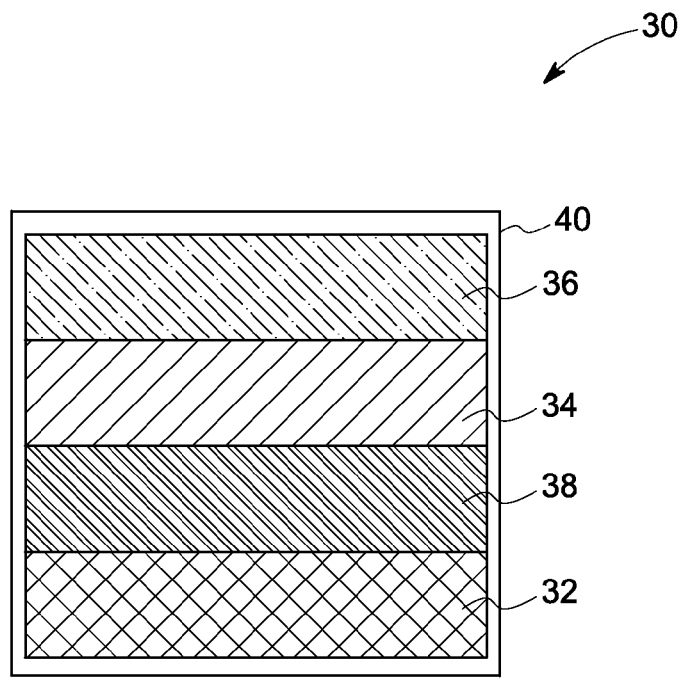
FIGS. 5-6 are cross-sectional views of yet another example of a colorimetric indicator, in accordance with aspects of the present disclosure.
Figure 6:
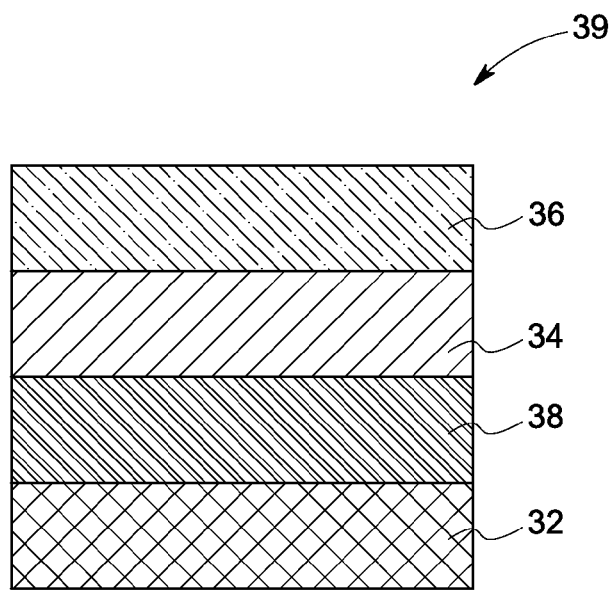

FIGS. 5-6 illustrate an alternative embodiment of the colorimetric indicator 20 of FIGS. 1-4. In the illustrated embodiment, a colorimetric indicator 30 may include an adhesive layer 32 made from POM, TPU or other plastic or labeling sticker material. The colorimetric indicator 30 may also include a colorimetric layer 34, and a barrier layer 36. In some embodiments, at least a portion of the colorimetric layer 34 may include a buffer agent. In the illustrated embodiments, another adhesive layer 38 may be disposed between the adhesive layer 32 and the colorimetric layer 34.

The adhesive layers 32 and 38 may be configured to attach the colorimetric layer 34 to the surface of the medical device body for, e.g., a surface of an ECG lead wire set. The adhesive layer 38 may be a combination of materials of the colorimetric layer 34 and the adhesive layer 32. The indicator 30 may be disposed in a packaging 40 that is configured to provide an environment that is substantially free of the external stimuli. Reference numeral 39 is generally representative of a portion of the colorimetric time indicator 30 without the packaging 40.

It should be noted that the colorimetric indicators of FIGS. 1-6 may be pre-fitted on the medical device. Alternatively, the colorimetric indicators of FIGS. 1-6 may be coupled to the existing devices any time before or immediately after the device is brought in use.

Figure 7:
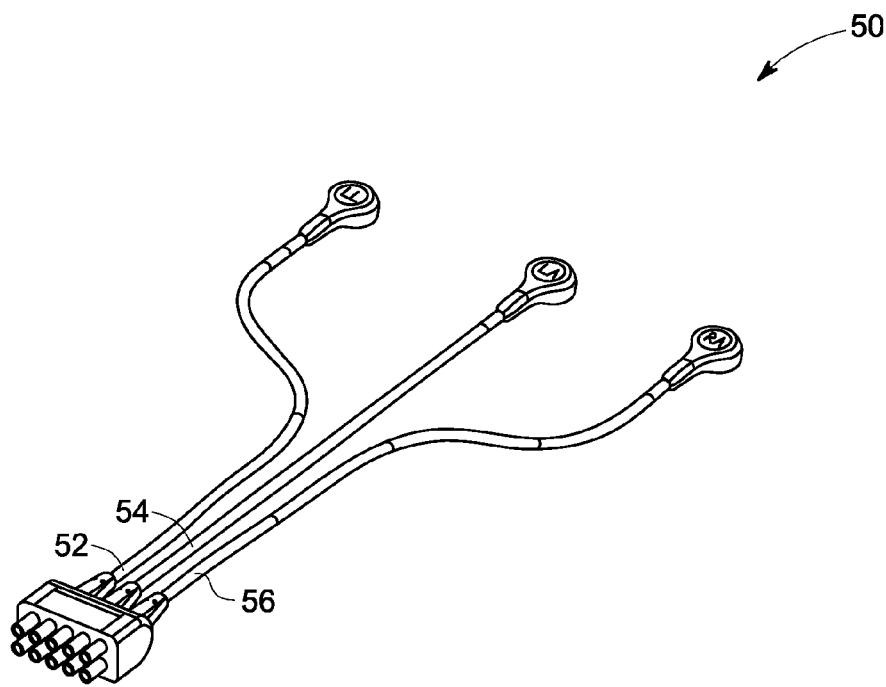
FIGS. 7-8 are perspective views of an example electrocardiograph (ECG) lead wire set configured for short term use, wherein the ECG lead wire set employs a colorimetric time indicator, in accordance with aspects of the present disclosure.
Figure 8:
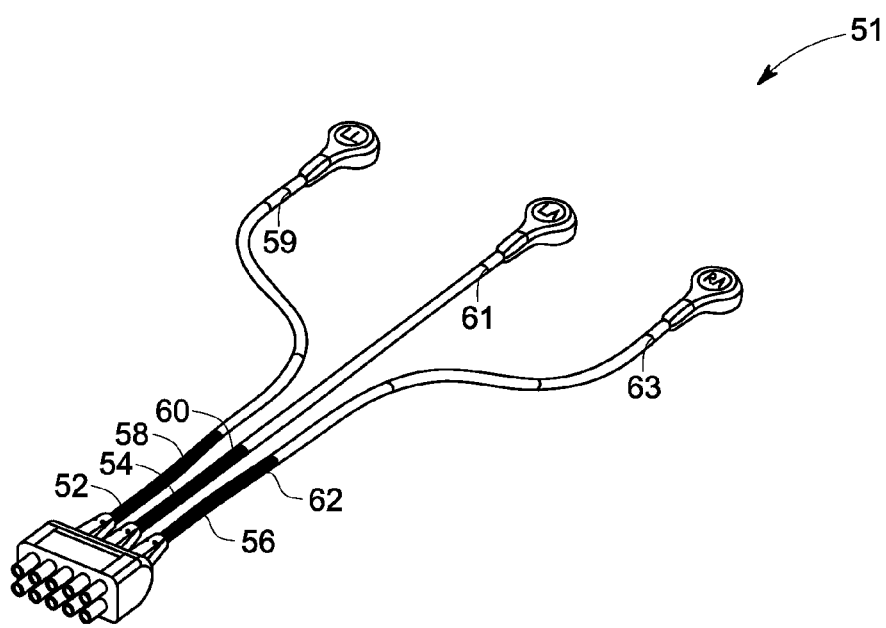

FIGS. 7-8 illustrate an example ECG lead-wire set 50 configured for short term use. In the illustrated embodiments, each of the individual lead-wires 52, 54 and 56 of the ECG-lead wire set 50 may include corresponding colorimetric indicators 58, 60 and 62. That is, the ECG lead-wire set employs two or more colorimetric indicators. Reference numeral 51 is generally representative of the lead-wire set 50 of FIG. 7 where each individual lead-wire has a corresponding colorimetric indicator. Although not illustrated, in some embodiments, the colorimetric indicators may be disposed in only some of the lead-wires 52, 54 and 56. The colorimetric indicators 58, 60 and 62 with the help of corresponding colorimetric layers may be configured to indicate individual time specificities using one or more visual indicators.

In one example, the colorimetric indicators 58, 60 and 62 may respond with a color change within a determined time upon exposure to oxygen in the air and moisture or only oxygen in the air. The colorimetric indicators 58, 60 and 62 may have substantially similar or different time specificities, as well as substantially similar or different response times. The indicators 58, 60 and 62 may be used as timelines ranging from minutes to days. The indicators 58, 60 and 62 may be disposed on the entire wire length or only a part of the lead-wire. In one example, as indicated by markers 59, 61 and 63, the different parts of the lead-wire set 51 may be assigned to indicate different use times, for example, the part 59 of the set 51 is assigned to have a time specificity of about 2 hours, the part 61 of the set 50 is assigned to have a time specificity of about 1 day, and the part 63 of the set 50 is assigned to have a time specificity of about 14 days. It should be noted that a gradual change in the visual indicator enables the indicators to continuously provide information representative of a time for which the device has been in use by grading the indicator in a suitable fashion. As illustrated in FIG. 8, upon exposure of the colorimetric indicator to the external stimuli, the colorimetric indicators 58, 60 and 62 indicate corresponding time specificities.

Figure 9:
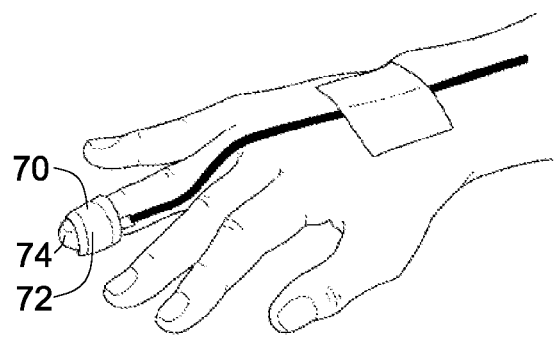
FIGS. 9-11 are perspective views of an example pulse oximeter ($SpO_2$) probe employing a colorimetric time indicator, in accordance with aspects of the present disclosure.
Figure 10:
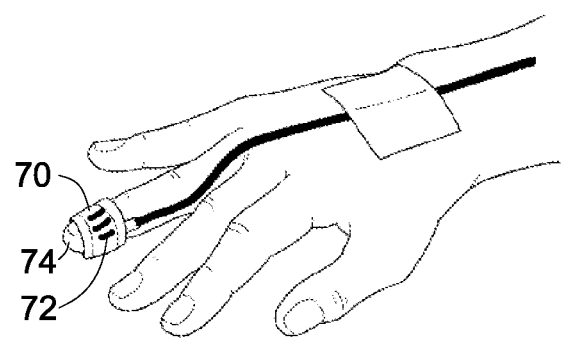
Figure 11:
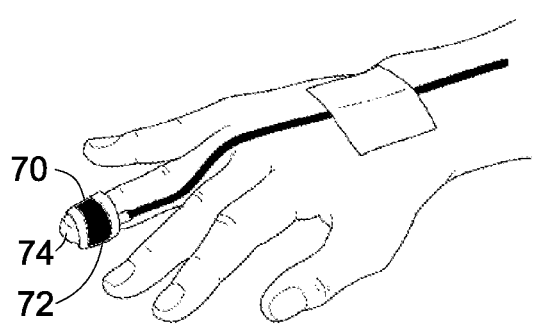

FIGS. 9-11 illustrate a single patient use pulse oximeter ($SpO_2$) probe 70. In certain embodiments, a colorimetric indicator 72 may be disposed on the $SpO_2$ probe 70 to indicate time specificity via a visual indicator upon exposure to the external stimuli. The probe 70 is configured to be used in a single procedure with a single patient. In one embodiment, the time scale of the $SpO_2$ probe 70 may be in a range from about few hours to about several days. In one embodiment, the colorimetric indicator 72 may include a colorimetric layer (not shown). The colorimetric layer may be disposed on at least a portion of the probe 70. The area of the probe that is coated with the colorimetric layer may be the visible area of probe end. FIG. 9 illustrates the $SpO_2$ probe 70 disposed on a finger 74 of the patient prior to exposure of the indicator 72 to an external stimulus, such as, but not limited to, carbon dioxide present in the air and/or moisture. In the illustrated embodiment of FIG. 9, the colorimetric indicator 72 may be in a passive stage. Although not illustrated, at least a portion of the colorimetric time indicator 72 may be disposed in a packaging.

FIG. 10 illustrates the $SpO_2$ probe 70 after exposure of the time indicator 72 to the external stimulus. In the illustrated embodiment of FIG. 10, the colorimetric indicator 72 may be in an active state. As illustrated in FIG. 10, the colorimetric indicator 72 is in the process of providing visual indicators while being exposed to the external stimulus.

FIG. 11 illustrates the $SpO_2$ probe 70 after an allowable usage time. As illustrated, the allowable usage time is indicated by a change in color or pattern of the colorimetric indicator 72.

In one example, the colorimetric indicator may be disposed on or in a flexible attachment mechanism of the $SpO_2$ probe. In this example, the colorimetric indicator may be disposed in a protective layer or packaging. The colorimetric indicator may be exposed to the external stimulus when the protective layer disintegrates after functional attachment of the probe to a user.

Figure 12:
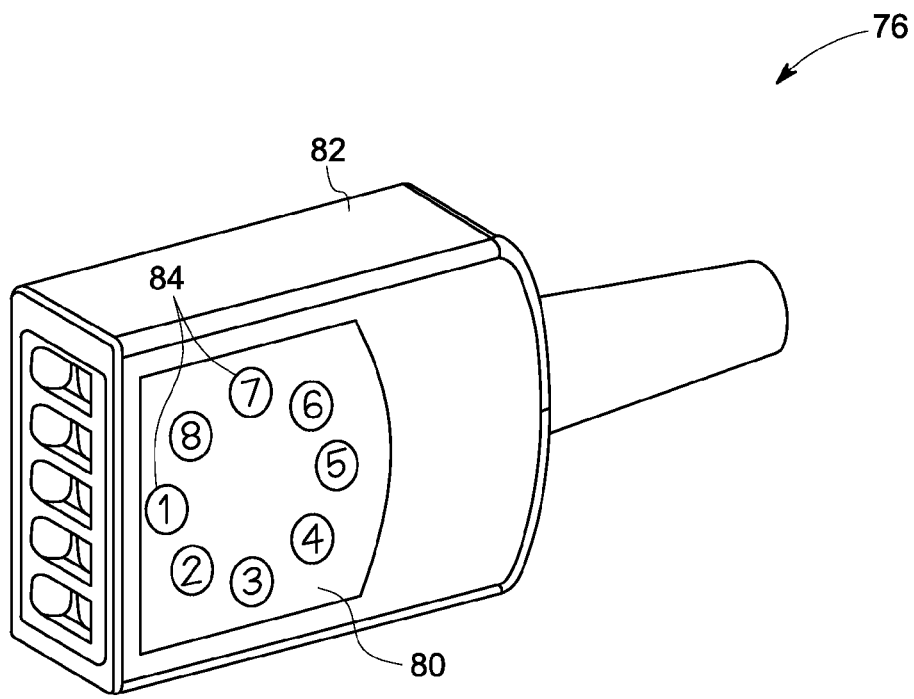
FIGS. 12-13 are perspective views of an example of a colorimetric time indicator configured to indicate time specificity via a visual indicator upon exposure to an external stimulus, in accordance with aspects of the present disclosure.
Figure 13:
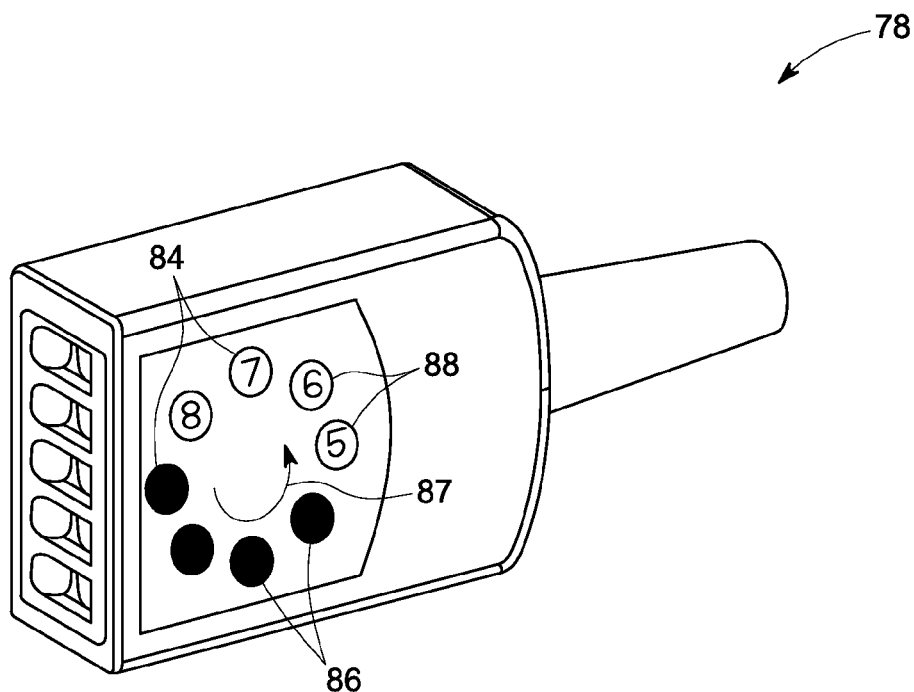

FIGS. 12-13 illustrate an example of a colorimetric time indicator 80 that is configured to indicate time specificity via a visual indicator upon exposure to an external stimulus. In particular, FIG. 12 depicts a diagrammatic representation of the colorimetric time indicator 80 in a passive state. Also, a diagrammatical representation 78 of the colorimetric time indicator 80 in an active state is illustrated in FIG. 13. In the illustrated embodiments, the colorimetric time indicator 80 is disposed on a medical probe 82. The colorimetric indicator 80 is configured to show a gradual progression of time using a plurality of portions 84. In the illustrated embodiment, the portions 84 are numbered 1 to 8. Each of the portions of the plurality of portions 84 may have corresponding time specificity. At least one portion of the plurality of portions 84 may have a time specificity that is different from the time specificities of the other portions 84. In one embodiment, each individual portion 84 may be configured to indicate a time specificity that is different than the time specificity of the other individual portions. Accordingly, the indicator 80 may be configured to indicate a gradual color change showing a number of days/hours the product has been in use till a given point in time. In one embodiment, the different portions 84 of the indicator 80 may have different amount of buffer agents, or different types of buffer agents, different amount of colorimetric materials, or different types of colorimetric materials so as to provide different time specificities.

In the illustrated embodiment of FIG. 12, the colorimetric indicator 80 is in the passive state; hence, in the illustrated embodiment of FIG. 12, the plurality of portions 84 does not indicate time specificities. In this illustrated embodiment, the device 82, such as, but not limited to, an ECG connector, may not be in use. However, in the illustrated embodiment of FIG. 13, the device 82 is in use, and the indicator 80 is in the active state, and the plurality of portions 84 is exposed to the external stimulus. The change in color of the colorimetric layer in a particular portion 84 may indicate an amount of time that has lapsed, thereby providing time specificity using a visual indicator. The colorimetric layer in the different portions 84 may be configured to indicate a change in color at different time intervals. Color change indicates that the product has been in use and healthcare professionals are aware of the risks related to re-using the product configured for single patient and single time use. In certain embodiments, the time scale may be tuned in a range from about minutes to about days. In one example, the time scale may be defined for example from one hour to 14 days. In another example, the time scale may be within a one hour scale.

Furthermore, as illustrated in FIG. 13, at a given point in time, some of the portions 86 of the plurality of portions 84 have indicated a time specificity using color change as the visual indicator, whereas, some other portions 88 of the plurality of portions 84 are yet to indicate the time specificity. As indicated by the arrow 87, the indicator 80 is configured to indicate time specificity in a gradually progressive manner. In one example, the different portions 84 may be configured to indicate time specificity at determined intervals of time. In this manner, at any given time within the desirable time period of the use of the device, the indicator 80 enables the user to determine the amount of time the device 82 has been in use. Although not illustrated, the available time-scale of the colorimetric indicator 80 may be in the form of numbers, charts or other graphical symbols.

Figure 15:
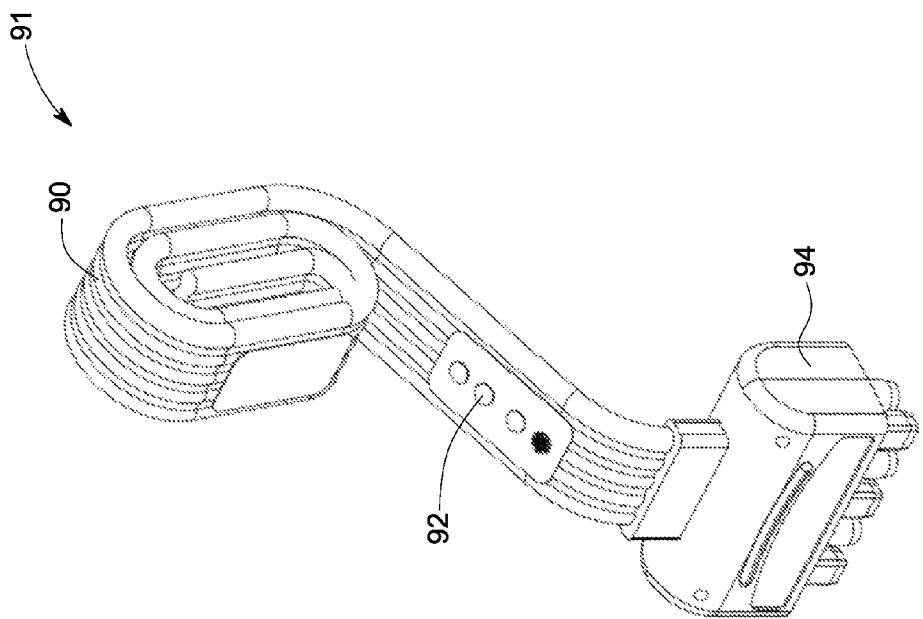
FIGS. 14-15 are perspective views of an example lead-wire cable employing a colorimetric time indicator, where the colorimetric time indicator is not disposed in a separate packaging, in accordance with aspects of the present disclosure.
Figure 14:
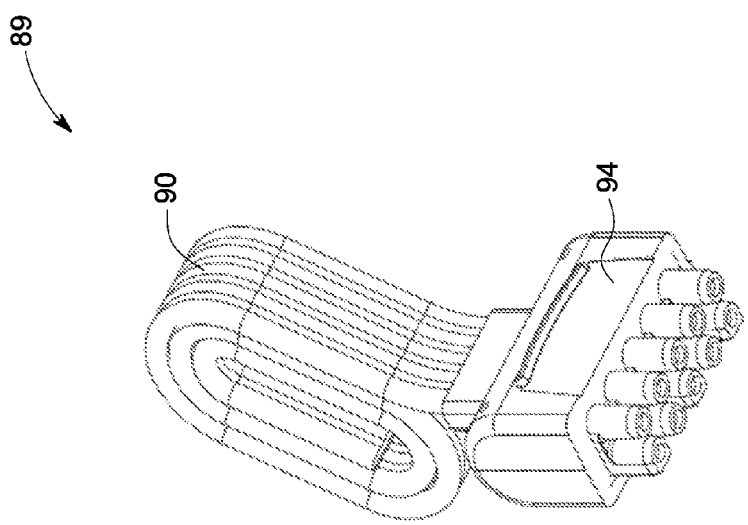

FIGS. 14-15 are perspective views 89, 91 of an example lead-wire cable 90 (e.g., ECG lead-wire cable) employing a colorimetric indicator 92. In particular, FIGS. 14-15 illustrate example embodiments 89, 91 where the colorimetric indicator is not disposed in a separate packaging. In the illustrated embodiment, a lead-wire cable 90 is configured to act as a packaging for the colorimetric indicator 92. Alternatively, although not illustrated, at least a portion of the lead-wire cable 90 and the indicator 92 may share the same packaging. In the illustrated embodiments, the colorimetric indicator 92 is disposed on a surface of the lead-wire cable 90. In one embodiment, the area where the indicator 92 is disposed may be air sealed or the packaging of the lead-wire cable 90 may be air sealed to prevent any undesirable interaction between the indicator 92 and the external stimulus.

In the illustrated embodiment of FIG. 14 where the lead-wire cable 90 is not in use, the lead-wire cable 90 is configured to provide an environment for the colorimetric time indicator 92 (see FIG. 15) that is substantially free of the external stimulus. Reference numeral 94 is generally representative of a medical device that is operatively coupled to the colorimetric indicator 92. That is, in the illustrated embodiment of FIG. 14, the time indicator 92 is in a passive state. In the illustrated embodiment of FIG. 15, as the lead-wire cable 90 is unfolded to use the device 94, the colorimetric time indicator 92 is exposed to the external stimulus present in the ambient environment. The colorimetric time indicator 92 transitions to an active state upon exposure to the external stimulus. In this embodiment, the lead-wire cable 90 may be unfolded immediately prior to commencing the use of the device 94. As a result of an exposure of the colorimetric indicator 92 to the ambient air and/or moisture, gradual color change commences.

In the illustrated embodiment, the lead-wire cable 90 may be folded and packaged in such a way, that when the device 94 is to be used, the cable 90 needs to be unfolded, and the packaging on the indicator area is disintegrated. As will be noted, the lead-wire cable 90 needs to be opened so that a connector on the monitor side is available to be connected to an interconnect cable or to a patient monitor.

Non-limiting examples of a colorimetric material for a colorimetric layer of the colorimetric indicator of the present technique may include dyes, such as, but not limited to food dyes. Non-limiting examples of food dyes other than methylene blue may include erioglaucine disodium salt, indigo carmine, fast green FCF, or combinations thereof. The erioglaucine disodium salt turns from light yellow to intense blue upon contact with air. Indigo carmine dye turns from light yellow to intense blue upon contact with air. Further, fast green FCF turns from light yellow to intense green upon contact with air.

In one example embodiment, methylene blue may be used in the colorimetric layer. Moreover, in one example, leuco methylene blue may be used as an oxygen exposure indicator. In one embodiment, the leuco methylene blue may be used with a buffer agent and/or a barrier layer to influence the time in which the leuco methylene blue may indicate a color change, or an amount of color change.

Figure 16:
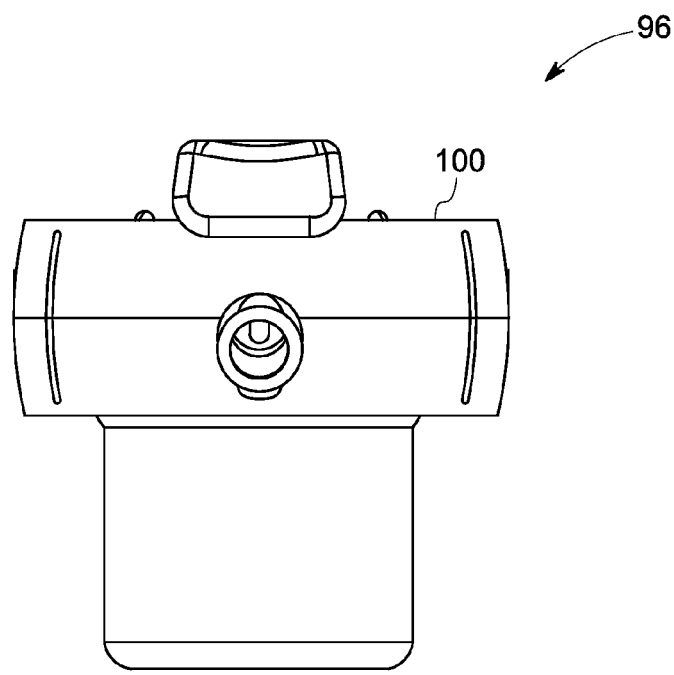
FIGS. 16-17 are perspective views of an example water trap having a colorimetric indicator to prevent use of the water trap after a desirable period, in accordance with aspects of the present disclosure.
Figure 17:
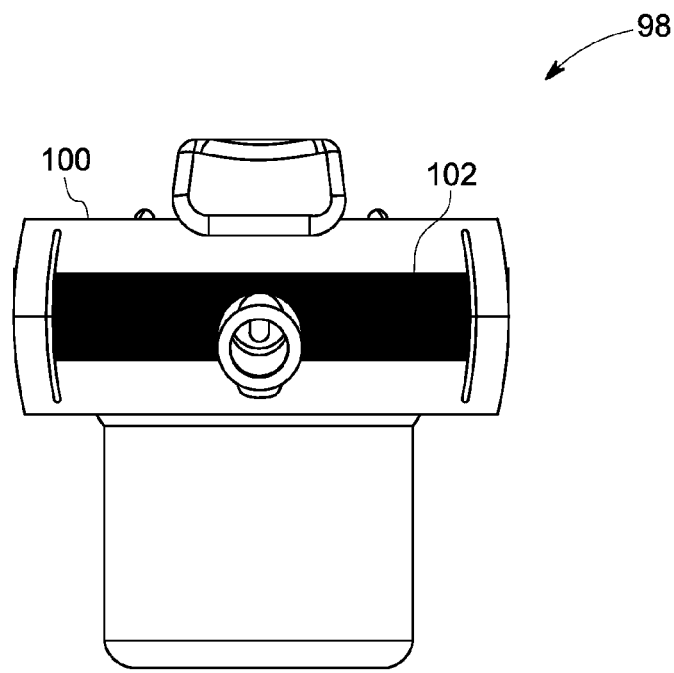

Turning now to FIGS. 16-17, perspective views 96, 98 of an example water trap 100 having a colorimetric indicator 102 are depicted. The colorimetric time indicator 102 may be disposed on the water trap 100 to prevent the use of the water trap 100 after a desirable period or the use time of the water trap 100. In one example, the colorimetric indicator 102 may be operatively coupled to the water trap 100 installed in an intensive care unit (ICU) to indicate a desirable usage time (e.g., 24 hours). In some embodiments, the colorimetric indicator 102 may be disposed at a visibly accessible area on the water trap 100. As illustrated in FIG. 17, after a determined usable time of the time 100, the colorimetric indicator 102 coupled to the water trap 100 indicates a color change, or a text or a symbol or other marks may become visible. The change in color may be gradual or sudden depending on one or more of the colorimetric material, buffer agent, and barrier layer.

Figure 18:
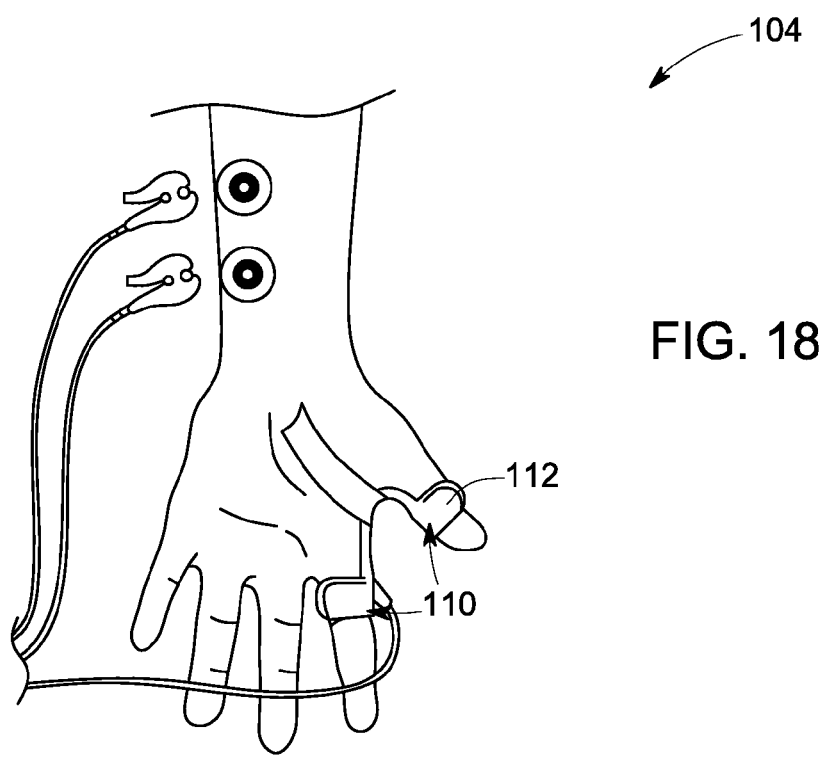
FIGS. 18-19 are perspective views of an example neuromuscular transmission (NMT) sensor that includes a colorimetric time indicator, in accordance with aspects of the present disclosure.
Figure 19:
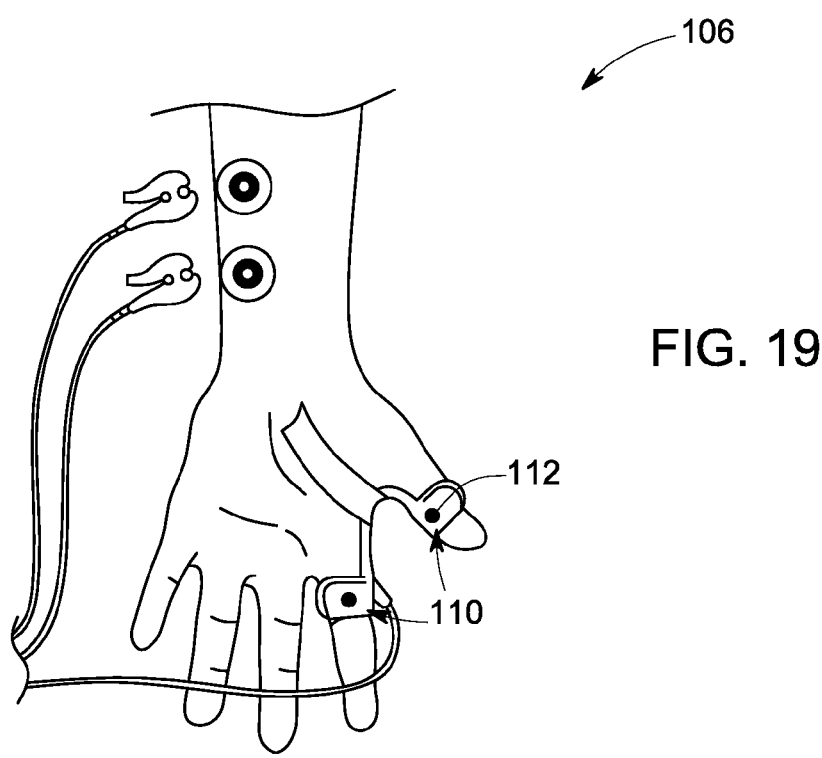
Figure 20:
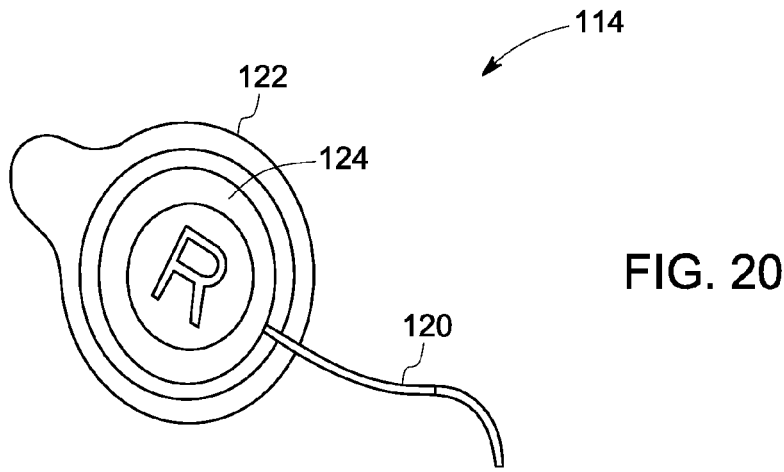
FIGS. 20-22 are perspective views of an example disposable ECG lead set having a disposable electrode, where a colorimetric time indicator is disposed on the electrode, in accordance with aspects of the present disclosure.
Figure 21:
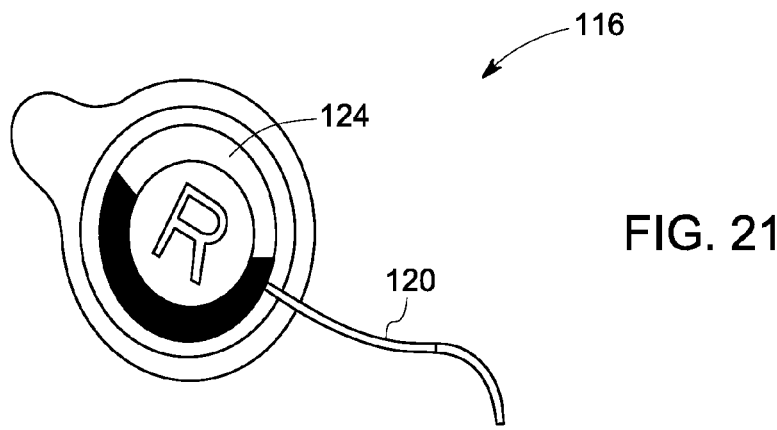
Figure 22:
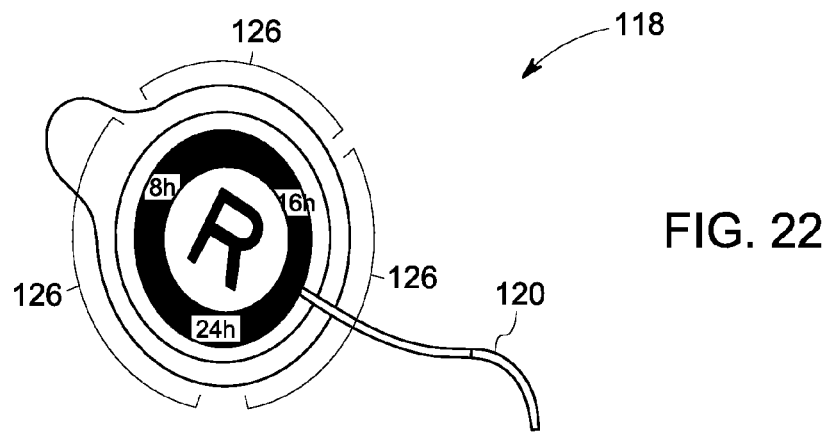

FIGS. 18-19 illustrate perspective views 104, 106 of an example neuromuscular transmission (NMT) sensor 110 that includes a colorimetric time indicator 112. A visible portion of the NMT sensor 110 may be coated with the colorimetric indicator 112. In one example, a time scale in an NMT sensor 110 may be from hours to several days. FIG. 18 illustrates the NMT sensor 110 with the colorimetric indicator 112 before exposure to oxygen in the air and moisture or only exposure to oxygen in the air. FIG. 19 illustrates the NMT sensor 110 with the colorimetric indicator 112 after exposure to oxygen in the air and moisture or only exposure to oxygen in the air Furthermore, FIGS. 20-22 illustrate perspective views 114, 116, 118 of an example disposable ECG lead set 120 having a disposable electrode 122. A colorimetric indicator 124 is disposed on the electrode 122. As will be appreciated, every electrode has determined position on the human body and identification is marked on the electrode using an electrode label with color and letter coding according to international and national standards, e.g., IEC or AAMI/AHA to represent the area on the human body where the electrode needs to be disposed. In the illustrated embodiment, the disposable electrode 122 and the integrated lead-wire 120 include a lead identification for positioning the disposable lead-set electrode 122 on the human body in a desirable fashion (correct way and position). As illustrated in FIG. 20, initially, the colorimetric indicator 124 may be disposed on the electrode 122 in a passive state. In the passive state the electrode 122 may be transparent to light, hence, the identification on the electrode is visible to be read by the user or the healthcare professional. When the packaging is taken off, and the active state of the indicator 124 sets in, the color changing process starts on the colorimetric layer of the indicator 124. The change in color of a colorimetric layer of the colorimetric indicator 124 may be instant or may be delayed depending on the chemical composition and use of the buffer layer in the colorimetric layer. The performance of the electrode 122 may weaken due to factors such as, but not limited to, presence of body secretions, such as sweat. Presence of such secretions weakens the ECG-signal when using attachable electrodes for the skin contact. The color change of the colorimetric layer may be controlled according to the usable lifetime of the electrode, which is determined to a certain time e.g., 24 hours. The color indication serves as a clock for electrode performance and indication for a need for a fresh electrode.

After the color changing period, the electrode label may not be identifiable, thereby preventing a second time use of the disposable lead-wire 120 with integrated electrodes. The healthcare personnel cannot identify the individual leads from each other anymore. Also, the electrode positioning coding is not readable anymore.

Moreover, as illustrated in FIGS. 21 and 22, the change in color in the active state of the indicator 124 may be gradual. Hence, even before the usable time, the indicator 124 can provide the information regarding the usage time of a medical device, such as the electrode 122. A plurality of regions 126 may be configured to have different time dependence for color change in dye. Although not illustrated, the colorimetric indicator may be configured to show color change in various patterns.

FIGS. 23(a)-(f) illustrate schematic representations of an example of a gradual color change in a disposable medical device employing a colorimetric time indicator 30. In the illustrated example, the colorimetric time indicator 130 is in an active state has a total time specificity of about 3 days. In the illustrated embodiment, the colorimetric indicator 130 illustrated in FIG. 23(a) may be disposed in a packaging and is in a passive state. In one embodiment, even if the indicator 130 is disposed on a medical device, the medical device may not be in use. In FIGS. 23(b)-(f), the colorimetric indicator 130 is in an active state. The colorimetric indicator 130 may be taken out of the packaging, and an instant reaction may occur indicated by a color change of the indicator 130. As illustrated in FIGS. 23(b)-(f), the time indicator 130 may be configured to indicate gradual progress of time and the number of days that the device has been in use. As represented by a dot 131, FIG. 23(c) indicates that the indicator has been in the active state for a determined period of time, e.g., 1 day, thereby indicating the use time of the device to be 1 day. The pattern on the indicator 130 may be any regular or irregular shape, such as, but not limited to, lines, numbers, charts or other graphical signs.

As indicated by dots 132, FIG. 23(d) indicates that the colorimetric time indicator 130 has been in the active state for a period of 2 days. Similarly, dots 133 in FIG. 23(e) indicate that the device has been in use for more than 2 days. Finally, dots 134 in FIG. 23(f) represent that the device has been in use for 3 days. In addition, as indicated in FIG. 23(f), as indicated, the colorimetric indicator 130 may be configured to display a message that may instruct the user to not use the device after the usable time of the device has come to an end or has expired.

FIG. 24 illustrates a flow chart 140 for providing a medical device having a colorimetric time indicator. At block 142, a disposable medical device is provided. The medical device may be a single patient use disposable device. At block 144, a colorimetric indicator is provided. Furthermore, at block 146, the colorimetric indicator is operatively coupled to the disposable medical device. Non-limiting examples of the ways to operatively couple the colorimetric indicator to the medical device may include printing the indicator on a label substrate and adhering the label substrate to the medical device; or directly printing the indicator on the medical device. Also, non-limiting examples of the type of substrate may include uncoated papers, gloss- and matte-coated papers, polyethylene (PE), polypropylene (PP), polyester (PET), and combinations thereof. Moreover, Non-limiting examples of printing techniques may include screen printing for flat surface, inkjet printing for flat surface, pad printing for curved surface, gravure printing, flexographic printing, or combinations thereof.

EXAMPLES

Example 1: Leuco Methylene Blue Solution A

The solution preparation was carried out in a nitrogen glove box. Methylene blue (1.36 g) and camphor sulfonic acid (0.68 g) are dissolved in Dowanol PM (14.87 g) by heating to ~80° C. on a hot plate. When the entire solid was completely dissolved, tin (II) 2-ethylhexanoate (5.88 g) was added by syringe. The resulting solution was stirred at 80° C. overnight and filtered to remove insoluble salt to give a yellow solution of leuco methylene blue (6.5 wt %)

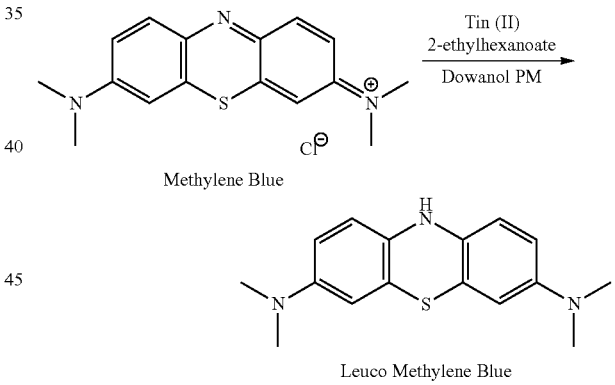

Example 2: Buffered Ink Solutions

The stock leuco methylene blue solution A is mixed with different amounts of ascorbic acid buffer and tetrabutylammonium hydroxide and diluted with Dowanol PM as in Table 1

TABLE 1

| Ex. | Leuco Methylene Blue solution A (uL) | Ascorbic acid Buffer (mg) | 40% Tetrabutylammonium hydroxide in water (uL) | Base to Ascorbic acid ratio | Dowanol PM (mL) | Induction time (h) | Transition time (h) |
|---|---|---|---|---|---|---|---|
| 1 | 200 | 400 | 0 | 0.0 | 10 | 5 | 11 |
| 2 | 200 | 400 | 600 | 1.5 | 10 | 1 | 10 |

TABLE 1-continued

| Ex. | Leuco Methylene Blue solution A (uL) | Ascorbic acid Buffer (mg) | 40% Tetrabutylammonium hydroxide in water (uL) | Base to Ascorbic acid ratio | Dowanol PM (mL) | Induction time (h) | Transition time (h) |
|---|---|---|---|---|---|---|---|
| 3 | 200 | 400 | 770 | 1.9 | 10 | 14 | 20 |
| 4 | 200 | 400 | 850 | 2.1 | 10 | 21 | 4 |
| 5 | 200 | 400 | 970 | 2.4 | 10 | 16 | 5 |
| 6 | 200 | 400 | 1070 | 2.7 | 10 | 13 | 7 |

Advantageously, the invention is cost effective, economical and easy to integrate to the current manufacturing processes and does not require any electricity to work so it could be used for low power solutions such as wireless measurements.

While only certain features of the invention have been illustrated and described herein, many modifications and changes will occur to those skilled in the art. It is, therefore, to be understood that the appended claims are intended to cover all such modifications and changes as fall within the scope of the invention.

The invention claimed is:

1. A method, comprising:
providing a disposable medical device, wherein the disposable medical device comprises a device used for monitoring and diagnosing cardiac function, a blood circulation device for measuring non-invasive blood pressure (NIBP), invasive blood pressure (IBP), body temperature, oxygen saturation, a hemoglobin measurement device, an anesthesia delivery device, a device for monitoring or determining brain functions, level of hypnosis, a device for measuring various parameters pertaining to body functions, or combinations thereof;
providing at least one colorimetric time indicator, comprising:
a colorimetric layer configured to indicate a time specificity via one or more visual indicators upon exposure to one or more external stimuli; and
operatively coupling the colorimetric time indicator to the disposable medical device, wherein the disposable medical device having the colorimetric time indicator is disposed in a packaging that provides an environment which is substantially free of the one or more external stimuli, wherein the one or more external stimuli comprise oxygen, carbon dioxide, or a combination thereof; and
changing a color of the colorimetric layer upon exposure to gamma radiation.

2. The method of claim 1, wherein operatively coupling the colorimetric time indicator to the disposable medical device comprises directly printing the colorimetric time indicator on a surface of the disposable medical device.

3. The method of claim 2, wherein printing comprises screen printing, inkjet printing, pad printing, gravure printing, flexographic printing, or combinations thereof.

4. The method of claim 2, wherein operatively coupling the colorimetric time indicator to the disposable medical device comprises:
disposing the colorimetric layer on a substrate; and
disposing the substrate on the surface of the disposable medical device.

5. The method of claim 2, wherein operatively coupling the colorimetric time indicator to the disposable medical device comprises:
disposing the colorimetric layer inside the disposable medical device such that when the disposable medical device is opened for use, the colorimetric time indicator is exposed to the one or more external stimuli.

6. The method of claim 2, wherein operatively coupling the colorimetric time indicator to the disposable medical device comprises:
disposing an adhesive material between the colorimetric time indicator and the disposable medical device.

7. The method of claim 2, wherein providing at least one colorimetric time indicator comprises:
providing two or more colorimetric time indicators, wherein each colorimetric time indicator of the two or more colorimetric time indicators is tailored for different time scales.

8. The method of claim 2, wherein providing a disposable medical device comprises:
providing a single patient single use device.

9. A method, comprising:
providing a colorimetric time indicator, comprising:
providing a colorimetric layer configured to be operatively coupled to a disposable medical device, wherein the colorimetric layer is configured to indicate a time specificity via one or more visual indicators upon exposure to one or more external stimuli; and
providing a packaging configured to provide an environment to the colorimetric layer, wherein the environment is substantially free of the one or more external stimuli, wherein the colorimetric layer is disposed in the packaging, wherein the one or more external stimuli comprise oxygen, carbon dioxide, moisture, ambient light, or combinations thereof; and
changing a color of the colorimetric layer upon exposure to gamma radiation.

10. The method of claim 9, wherein providing a colorimetric layer comprises providing the colorimetric layer comprising one or more buffer agents configured to facilitate tunability of the time specificity, and wherein the one or more buffer agents are disposed at least in part in the colorimetric layer.

11. The method of claim 10, wherein the one or more buffer agents comprise a reducing buffer agent.

12. The method of claim 10, wherein the one or more buffer agents comprise reducing saccharides, E301 sodium ascorbate, E302 calcium ascorbate, E303 potassium ascorbate, or combinations thereof.

13. The method of claim 9, further comprising:
providing a barrier layer configured to facilitate tunability of the time specificity, wherein the barrier layer is disposed on at least a portion of the colorimetric layer.

14. The method of claim 13, wherein providing a barrier layer comprises providing the barrier layer comprising a determined permeability rate for the one or more external stimuli.

15. The method of claim 13, wherein providing a barrier layer comprises providing the barrier layer comprising polyester, poly-vinylidene chloride, poly(methyl methacrylate) (PMMA), polycarbonate, polystyrene, polyolefin, or combinations thereof.

16. The method of claim 9, wherein providing a colorimetric layer comprises providing the colorimetric layer in a passive state.

* * * * *